(12) United States Patent
Schlaudraff et al.

(10) Patent No.: US 10,533,931 B2
(45) Date of Patent: Jan. 14, 2020

(54) METHOD AND EXAMINATION SYSTEM FOR EXAMINING AND PROCESSING A MICROSCOPIC SAMPLE

(71) Applicant: Leica Microsystems CMS GmbH, Wetzlar (DE)

(72) Inventors: Falk Schlaudraff, Butzbach (DE); Blagovesta Wegner, Wetzlar (DE)

(73) Assignee: LEICA MICROSYSTEMS CMS GMBH, Wetzlar (DE)

(*) Notice: Subject to any disclaimer, the term of this patent is extended or adjusted under 35 U.S.C. 154(b) by 9 days.

(21) Appl. No.: 15/574,492

(22) PCT Filed: May 20, 2016

(86) PCT No.: PCT/EP2016/061494
§ 371 (c)(1),
(2) Date: Feb. 19, 2018

(87) PCT Pub. No.: WO2016/185040
PCT Pub. Date: Nov. 24, 2016

(65) Prior Publication Data
US 2018/0149561 A1    May 31, 2018

(30) Foreign Application Priority Data

May 20, 2015  (DE) .................. 10 2015 108 017

(51) Int. Cl.
*G01N 1/28* (2006.01)
*G02B 21/36* (2006.01)
(Continued)

(52) U.S. Cl.
CPC ........... *G01N 1/286* (2013.01); *G02B 21/365* (2013.01); *G06T 7/73* (2017.01);
(Continued)

(58) Field of Classification Search
None
See application file for complete search history.

(56) References Cited

U.S. PATENT DOCUMENTS

| 2003/0133190 A1 | 7/2003 | Weiss |
| 2004/0085443 A1 | 5/2004 | Kallioniemi et al. |
| (Continued) | | |

FOREIGN PATENT DOCUMENTS

| AT | 505669 A4 | 3/2009 |
| DE | 102012214664 A1 | 2/2014 |
| (Continued) | | |

*Primary Examiner* — Christopher Braniff
(74) *Attorney, Agent, or Firm* — Leydig, Voit & Mayer, Ltd.

(57) ABSTRACT

A method for examining and processing a microscopic sample arranged on a slide includes producing reference markings on the slide by a laser beam of a laser microdissection system. A digital image of the sample and the reference markings on the slide is produced by a digital optical imaging device. An image region is defined and first position information data which indicate a position of the image region is generated. The reference markings are identified in the image and second position information data which indicate a position of the reference markings in the image is generated. The reference markings are identified, and third position information data which indicate the position of the reference markings in the laser microdissection system is generated. The first, second and third position information data are correlated and a sample region which corresponds to the image region is processed.

18 Claims, 3 Drawing Sheets

(51) Int. Cl.
*G06T 7/73* (2017.01)
*G02B 21/34* (2006.01)
(52) U.S. Cl.
CPC ...... *G01N 2001/2886* (2013.01); *G02B 21/34* (2013.01); *G06T 2207/10056* (2013.01); *G06T 2207/30204* (2013.01)

(56) References Cited

U.S. PATENT DOCUMENTS

| | | |
|---|---|---|
| 2004/0252291 A1 | 12/2004 | Schutze |
| 2011/0194749 A1* | 8/2011 | Morris .................. G01N 1/286 382/133 |
| 2012/0045790 A1 | 2/2012 | Van Dijk et al. |
| 2013/0278941 A1 | 10/2013 | Loerch |
| 2013/0327195 A1 | 12/2013 | Routamaa et al. |
| 2014/0049818 A1 | 2/2014 | Schlaudraff |
| 2014/0098214 A1 | 4/2014 | Schlaudraff et al. |
| 2016/0202040 A1 | 7/2016 | Schlaudraff et al. |

FOREIGN PATENT DOCUMENTS

| | | |
|---|---|---|
| DE | 102013217532 A1 | 3/2015 |
| EP | 1276586 B1 | 1/2003 |
| WO | WO 2008080403 A1 | 7/2008 |
| WO | WO 2014053955 A1 | 4/2014 |
| WO | WO 2015028401 A1 | 3/2015 |

* cited by examiner

METHOD AND EXAMINATION SYSTEM FOR EXAMINING AND PROCESSING A MICROSCOPIC SAMPLE

CROSS-REFERENCE TO PRIOR APPLICATIONS

This application is a U.S. National Stage Application under 35 U.S.C. § 371 of International Application No. PCT/EP2016/061494 filed on May 20, 2016, and claims benefit to German Patent Application No. DE 10 2015 108 017.6 filed on May 20, 2015. The International Application was published in German on Nov. 24, 2016 as WO 2016/185040 A1 under PCT Article 21(2).

FIELD

The present invention relates to a method and to an examination system for examining and processing a microscopic sample.

BACKGROUND

Methods for processing microscopic samples or objects by laser microdissection have been in existence since the mid-1970s and have continuously been developed further since then.

In laser microdissection, cells, tissue regions, etc. can be isolated from a tissue complex and obtained as dissectates. A particular advantage of laser microdissection is that the tissue is in contact for a short time with the laser beam, by which the tissue next to the laser beam is scarcely altered. The dissectates can specifically be obtained in different ways.

For example, a dissectate can be isolated from a sample by means of an infrared or ultraviolet laser beam and falls into a suitable dissectate collector under the influence of gravity. The dissectate can in this case also be cut out of the sample together with an adhering membrane.

Another method is laser capture microdissection. In that method, a thermoplastic membrane, which may also be connected to a reaction vessel, is heated by means of a corresponding laser beam. The membrane melts with the desired region of the object and can be removed in a subsequent step. A further alternative consists in sticking the dissectate to a cap of a dissectate collector by means of the laser beam. Inverted microscope systems for laser microdissection are also known.

Known microscope systems for laser microdissection have a reflected light device, into the beam path of which a laser beam is coupled. The laser beam is focused by the particular microscope objective used onto the sample, which is lying on a microscope stage which can be displaced automatically by means of a motor. A cut line is produced, for example, by displacing the microscope stage during cutting in order to move the sample relative to the fixed laser beam. However, this has the disadvantage, inter alia, that the sample cannot be observed properly during production of the cut line because it moves in the field of view.

More advantageous laser microdissection systems therefore have laser scanning devices which are configured correspondingly to displace the laser beam or the point of impact thereof on the sample, which is then fixed. Such laser microdissection systems also have particular advantages in the context of the present invention. A particularly advantageous laser microdissection system of the type mentioned, which has a laser scanning device with wedge prisms, is described in EP 1 276 586 B1.

In both cases, that is to say both in laser microdissection systems in which the microscope stage is displaced and in laser microdissection systems which have a laser scanning device, the operation is generally carried out using pulsed lasers, a hole being produced in the sample by each laser pulse. A cut line forms by stringing such holes together, optionally with overlapping.

In microscopic examination methods, for example in medical diagnostics, magnifying digital optical imaging devices, in particular slide scanners, are frequently used in addition to microscopes in the narrower sense. Slide scanners are used to produce partial or complete images of slides with microscopic samples applied thereto, which images can then be evaluated on a screen and/or stored. The evaluation can also be made partially or fully automatically, for example using pattern recognition methods by means of which, for example, pathologically altered cell or tissue types can be identified. A slide scanner thus permits examination or diagnosis on the basis of digital images of samples without the direct use of a microscope. Slide scanners have the advantage of a high throughput and allow a large number of samples to be processed largely automatically.

If cell or tissue types requiring additional molecular-biological and/or biochemical investigation are detected in digital images of a corresponding digital optical imaging device, for example a slide scanner, corresponding regions of a microscopic sample can be processed in a laser microdissection system, that is to say can be cut out of the sample in such a system.

However, the subsequent processing by laser microdissection of samples which have previously been examined by means of magnifying digital optical imaging devices, for example the mentioned slide scanners, is conventionally found to be highly complex. In particular, it is conventionally not possible to define specific regions on the basis of a digital image of a microscopic sample and process exactly the same regions of the same object or slide in a laser microdissection system.

Instead, the prior art in this context is the production of serial sections, as disclosed, for example, in US 2012/0045790 A1. In this case, two adjacent thin tissue sections are prepared from a tissue block, for example by means of a microtome, and treated differently. The first section is subjected to a standard treatment and subsequent production of a corresponding image. Staining of the sample and digitization in a slide scanner are carried out, for example. On the basis of this section, a pathologist selects sample regions for examination in a laser microdissection system. Corresponding region information is stored in a laboratory information system. The second section is supplied in parallel to the laser microdissection system. In the laser microdissection system, this second section is then processed on the basis of the region selection made in respect of the first section. Digital image overlay programs, which are comparatively slow and are not sufficiently accurate for reliable results, may also be used in this connection.

SUMMARY

In an embodiment, the present invention provides a method for examining a microscopic sample arranged on a slide using a magnifying digital optical imaging device, by which the sample is optically imaged and a digital image of the sample is produced, and for processing the microscopic sample arranged on the slide by a laser microdissection system which has an optical microscope and a laser and with which a laser beam for processing the sample is produced. The method includes the steps: a) producing at least two reference markings on the slide by the laser beam of the laser microdissection system, the reference markings being identifiable both by the digital optical imaging device and by the laser microdissection system; b) applying the sample to the slide, before or after the reference markings are produced on the slide in accordance with step a); c) producing a digital image of the sample on the slide by the digital optical imaging device, wherein the image also includes the reference markings; d) defining at least one image region of the image and generating first position information data which indicate a position of the at least one image region in the image; e) identifying the reference markings in the image and generating second position information data which indicate a position of the reference markings in the image, before, during or after the at least one image region of the image is defined in accordance with step d); f) providing the first and second position information data to the laser microdissection system; g) imaging the slide having the sample and the reference markings and identifying the reference markings by the laser microdissection system, and generating third position information data which indicate the position of the reference markings in the laser microdissection system; and h) correlating the first position information data, the second position information data and the third position information data, and processing at least one sample region of the sample which corresponds to the at least one image region of the image defined in step d), by the laser microdissection system.

BRIEF DESCRIPTION OF THE DRAWINGS

The present invention will be described in even greater detail below based on the exemplary figures. In the drawings, elements which correspond to one another are shown with identical reference numerals and are not described repeatedly. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
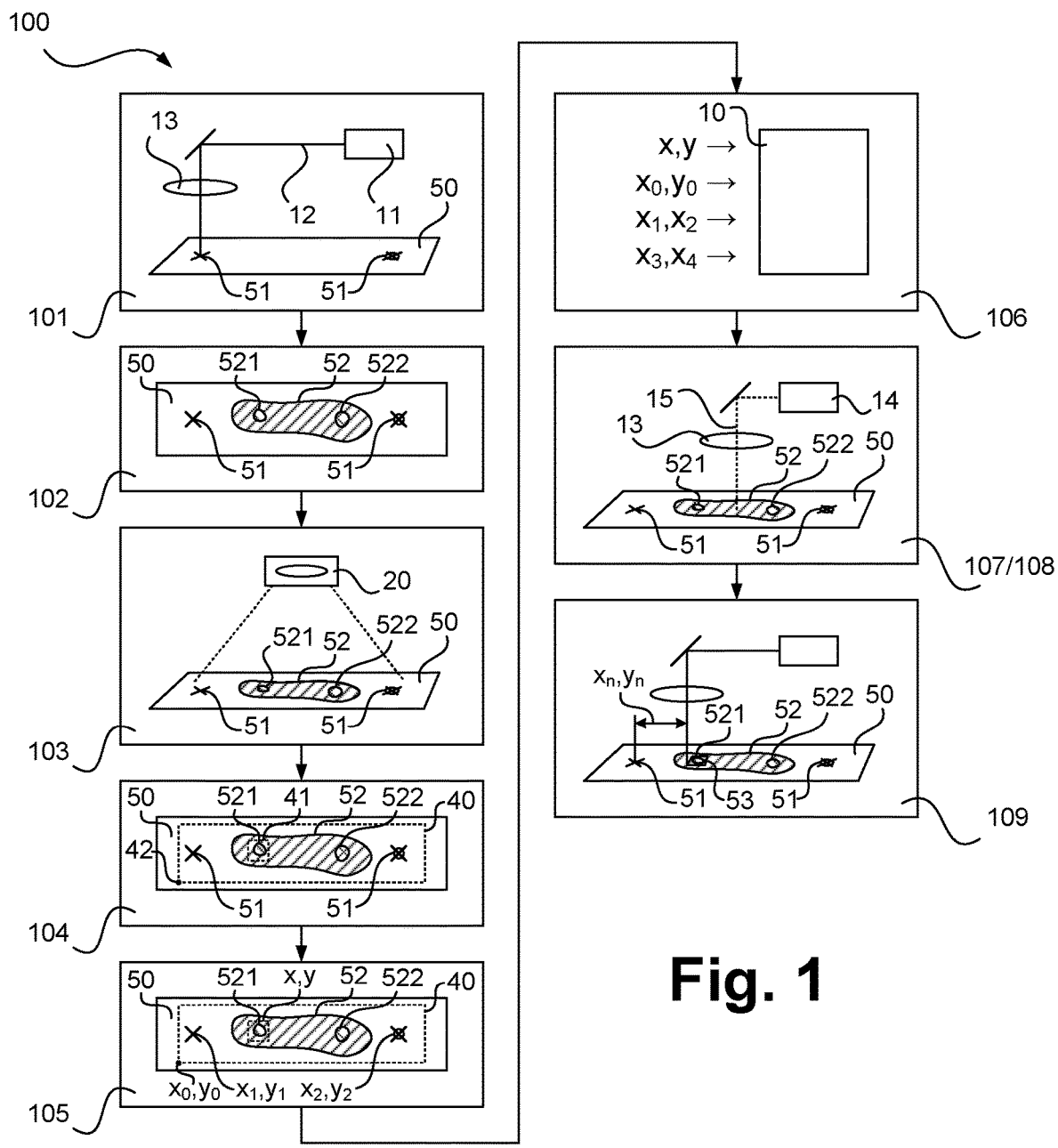
FIG. 1 schematically shows a method according to an embodiment of the invention.

The inventors have recognized that corresponding methods have the disadvantage in particular that a corresponding tissue region is not located accurately on the second section in the laser microdissection system. This is also explained in greater detail within the scope of the following description.

Embodiments of the present invention provide for improved examination possibilities for the examination and processing of microscopic samples, in particular using the mentioned magnifying digital optical imaging devices and laser microdissection systems.

Embodiments of the present invention provide a method and an examination system for examining and processing a microscopic sample.

An embodiment of the invention starts from a method for examining a microscopic sample arranged on a slide by means of a magnifying digital optical imaging device, by means of which the sample is imaged by optical means and a digital image of the sample is produced, and for processing the microscopic sample arranged on the slide using a laser microdissection system which has an optical microscope and a laser unit, and with which a laser beam for processing the sample is produced.

An embodiment of the invention relates to such a method which comprises the following steps:

a) producing at least two reference markings on the slide by means of the laser beam of the laser microdissection system, which reference markings can be identified both by means of the digital optical imaging device and by means of the laser microdissection system, b) applying the sample to the same slide, before or after the reference markings are produced on the slide in accordance with the above-mentioned step a), c) producing the digital image of the sample on the slide by means of the digital optical imaging device, wherein the image also includes the reference markings, d) defining at least one image region of the image and generating first position information data which indicate the position of the at least one image region in the image, e) identifying the reference markings in the image and generating second position information data which indicate the position of the reference markings in the image, before, during or after the at least one image region of the image is defined in accordance with the above-mentioned step d), f) providing the first and second position information data to the laser microdissection system, g) imaging the slide having the sample and the reference markings and identifying the reference markings by means of the laser microdissection system, and generating third position information data which indicate the position of the reference markings in the laser microdissection system, h) correlating the first position information data, the second position information data and the third position information data and processing at least one sample region of the sample, which corresponds to the at least one image region of the image defined in the above-mentioned step d), by means of the laser microdissection system.

Thus, according to an embodiment of the invention, at least two reference markings which can be identified by means of the imaging device and the laser microdissection system are first produced on the slide by means of the laser beam of the laser microdissection system. Because the reference markings are produced by means of the laser of the laser microdissection system, no additional marking means or separate marking devices are required. Thus, unlike in known methods, slides already provided with reference markings, as are known, for example, from DE 10 2012 241 664 A1, are not or are not necessarily used within the context of the present invention.

Before or after the reference markings are produced on the slide in accordance with the step just discussed, the sample is applied to the same slide and optionally subjected to a suitable treatment on the slide. The sample can be fixed, stained or dewatered, for example, after it has been applied to the slide.

Within the context of an embodiment of the present invention, a digital image both of the sample and of the reference markings previously produced on the slide is then produced by means of the imaging device provided separately to the laser microdissection system, for example in a different location. The slide is thus digitized by means of a digital optical imaging device, for example by means of a slide scanner, whereby a digital image is obtained which includes the sample itself (or optionally only a portion thereof) and the reference markings.

According to an embodiment of the invention, it is further provided to define at least one image region of such an image, for example by examination by a pathologist or by means of an automatic examination method, and to generate first position information data which indicate the position of the at least one image region in the image. This step corresponds to methods which are conventional per se, in which a pathologist manually marks specific regions, for example pathogenically altered tissue regions, in a sample section or the digital image thereof, for example encircles them with a marking line. The definition of corresponding image regions can also take place partially or fully automatically, as mentioned, for example, using pattern or tissue recognition methods.

The "position information data" which indicate the position of the at least one image region in the image are, for example, digital data which correspond to a corresponding marking line and can be provided and optionally stored temporarily in a manner known per se, for example using XML files. A "position" of the at least one image region in the image includes, as used in this application, the position in the image, for example of one or more points, but also a geometric or irregular form which can be specified as desired by a user or by means of a corresponding recognition specification.

Within the context of the method according to an embodiment of the invention, before, after or at the same time as the at least one image region of the image is defined and the first position information data are generated, the reference markings are identified in the image and second position information data, which indicate the position of the reference markings in the image, are generated. Identification of the reference markings can also be carried out manually, for example by a pathologist marking the reference markings in a given manner, for example by means of a cross, in a corresponding image by means of a mouse or other digital input unit. Alternatively, however, it can also be provided in this case to identify the reference markings in the image by means of automatic recognition specifications.

For this purpose, the reference markings can have a predetermined form, with which they were produced previously by means of the laser microdissection system. It can further be expedient to make the at least two reference markings different and to record the form of the first, second, etc. reference marking. This difference in form assists in identifying the sequence of the reference markings. For example, they may be cross-shaped or in the form of crosshairs. The second position information data can in principle be provided and optionally stored temporarily in the same manner as the first position information data, that is to say, for example, in the form of XML files.

The method according to an embodiment of the invention provides that the first position information data and the second position information data (and optionally further position information data in the corresponding order) are supplied to the laser microdissection system, and the slide previously digitized, that is to say used for generating the digital image in the imaging device, with the sample applied thereto, is introduced into the laser microdissection system, where it is imaged again. It is of course also possible, for example, first to digitize a series of slides in the imaging device and to store them temporarily. The slide or slides can be kept under suitable storage conditions. It is thus not expressly necessary within the context of the present method that a slide is introduced into the laser microdissection system immediately after production of the digital image or after diagnosis, that is to say after the definition of at least one image region of the image or the identification of the reference markings in the imaging device. The slide having the sample can be introduced into the laser microdissection system and imaged therein immediately before an examination that is to be carried out, so that the sample can be protected. For imaging in the laser microdissection system there is used, for example, a digital or partially digital imaging system present therein.

The reference markings are then identified again by means of the laser microdissection system. In this case too, the procedure may be partially or fully manual or partially or fully automatic. In each case, during or after the identification of the reference markings, third position information data, which indicate the position of the reference markings in the laser microdissection system, are generated. Corresponding position information data can again be provided the same as or different from the first and second position information data.

According to the invention, it is then possible to correlate the first, second and third position information data. It is possible in particular to relate the second and third position information data with one another, so that a shift, twisting, displacement, etc. of a corresponding slide in a laser microdissection system can be compensated for. The second and third position information data each relate, as mentioned, to the reference markings on a corresponding slide, so that a position correction takes place simply and without difficulty in particular with identical magnification. The accuracy with which the slide is positioned before the image is produced in the imaging device and before processing in the laser microdissection system can therefore be comparatively low. In particular, it is not important whether a slide was slightly twisted or displaced when it was introduced into the imaging device or the laser microdissection system. Even in the case of different magnifications of the image taken in the imaging device and in the laser microdissection system, simple conversion is generally possible by increasing or reducing (scaling) position information data. When a corresponding position correction has taken place, the laser microdissection system knows, because the first position data are advantageously correspondingly corrected at the same time, the exact location on a corresponding slide of the sample region of the sample that corresponds to the at least one image region of the image of the sample defined on the basis of the image of the imaging device. Thus, within the context of the present invention, the first position information data, which relate to the image region corresponding to a sample region in the sample, can advantageously be corrected, for example, by correction factors resulting from the correlation of the second and third position information data.

In this manner it is always possible to process in the laser microdissection system, for example to cut out by means of a laser, the exact sample region that was previously defined in the image as the imaging region, for example by a pathologist or by digital, image-data-processing software.

Embodiments of the invention overcome a number of disadvantages of the prior art. Conventionally it is necessary, as described with reference to US 2012/0045790 A1, to prepare serial sections, which involves a considerable additional outlay (preparation of two sections, repeated staining and use of two slides), which is not tolerable in particular in routine diagnostics. This is the case in particular in view of the fact that not every section in diagnostics is recognized as being in need of investigation. Parallel sections which do not have to be processed by means of the laser microdissection system are thus produced unnecessarily. If serial sections are only produced when the need for investigation has been established, this requires a sample to be processed again, which is time-critical and involves the potential for mistakes. In addition, the sample must be correspondingly stored.

A further disadvantage of the use of serial sections is the transfer of the cut lines, which are comparatively easy to define on a standard slide but are very difficult to transfer to a serial section which is stained differently or not stained at all and in particular is not covered with a coverslip. Two sections, that is to say corresponding microscopic samples, are generally oriented slightly differently on the slide; furthermore, the cutting operation and subsequent processing steps lead to compression of the tissue and to the production of dissection artifacts. According to the prior art, the use of complex image overlay methods is therefore required, which, as mentioned, are slow and may be susceptible to error. Furthermore, smaller sample regions in particular, such as metastases, are not equally pronounced in serial sections.

By contrast, by the use of the reference markings in the manner described, an embodiment of the present invention provides an accurate and inexpensive solution, suitable for large-scale use, for the scanning of slides and the subsequent selection of specific samples or sample regions for laser microdissection and subsequent biochemical or molecular biological examination methods. For example, in contrast to DE 10 2012 214 664 A1, in which it is proposed to use slides which are already provided with markings, these markings are, as mentioned, produced within the context of the present invention simply and inexpensively in the laser microdissection system itself. The production of the reference markings in the laser microdissection system can take place at a defined magnification, as is also used, for example, in the subsequent digital acquisition and production of the digital image. Furthermore, by specifically producing reference markings, the abilities of a digital imaging device to identify corresponding reference markings can be considered. The reference markings can thus be produced by means of the laser microdissection system in any desired manner, for example in order that they are particularly easily locatable.

A major advantage of an embodiment of the present invention over the use of slides with reference markings already applied thereto, as in DE 10 2012 214 664 A1, for example, is its universal usability with any desired glass or membrane slides. The cost benefit of the method according to the invention is therefore considerable. Within the context of an embodiment of the present invention, the reference markings can be produced on the slide by means of the laser microdissection system, as already mentioned, before the sample is applied. This can be advantageous in particular when the reference markings are produced on a slide, or on a corresponding substrate, which is later covered by a layer that cannot be marked by the laser microdissection system.

It is advantageous in particular if the reference markings are produced on the basis of fourth position information data which specify a position of the reference markings on the slide. Corresponding fourth position information data can also be used, for example, for a plurality of slides in an identical manner, so that an identical or at least comparable marking of a plurality of slides is possible. This can simplify the location of corresponding reference markings on different slides, for example, because in such a case such reference markings can be sought by means of the imaging device in specific, prior-known regions of a corresponding image. This likewise also applies to the location of the reference markings in the laser microdissection system. It is therefore advantageous if the reference markings in the image and/or the laser microdissection system are identified using the fourth position information data.

As mentioned, it is possible within the context of an embodiment of the present invention to use a slide which is made at least in part of glass or metal or plastics material and/or which has a membrane, wherein the reference markings are produced in the glass or metal or plastics material and/or in the membrane. Production of the reference markings can also include, for example, an adjustment of laser beam properties of a corresponding laser microdissection system, wherein, for example, a particularly high laser power is specified for the processing of glass or metal or plastics material.

As likewise mentioned, identification of the reference markings can in each case be carried out at least in part by means of automatic methods; it can, however, also be carried out manually. Carrying out an automatic method permits particularly reproducible location of corresponding reference markings without the risk of misinterpretation by a user.

In a method according to an embodiment of the invention, as likewise mentioned, the at least one image region of the image is advantageously defined by manual and/or automatic drawing of a cut line that is to be used by the laser microdissection system, which cut line represents a limiting line in a corresponding image. In this connection, methods known per se for defining and processing corresponding cut lines can be used, for example.

As likewise mentioned, it is advantageous if the first position information data also include, in addition to a pure geometric position, a geometric form, for example, of the at least one image region of the image. This form may also be irregular and defined in any desired manner.

An embodiment of the present invention extends also to an examination system which is configured for examining and processing a microscopic sample arranged on a slide and which has a magnifying digital optical imaging device, which images the sample by optical means and produces a digital image of the sample, and a laser microdissection system, which has an optical microscope and a laser unit, which produces a laser beam for processing the sample.

The examination system is distinguished by control means which are configured to control the digital optical imaging device and the laser microdissection system and to control and/or execute and/or operate a method as described hereinbefore.

In particular, the control means of the examination system comprise software which is installed on the magnifying digital optical imaging device and/or on the laser microdissection system.

According to a particularly preferred embodiment of the invention, the examination system preferably also comprises a data transfer device for providing the first and second position information data to the laser microdissection system.

An embodiment of the present invention also provides software which is designed to control and/or execute and/or operate an above-described method.

In order to avoid misunderstandings, it should be emphasized at this point that the method used within the context of an embodiment of the invention, or the corresponding examination system, is explicitly used with samples which are already prepared to be suitable for microscopy. They may be, for example, thin sections removed from a larger tissue block, for example a fixed organ or a biopsy of a corresponding organ, by means of a microtome. The present invention therefore is not used for obtaining corresponding samples but for examining and processing them, in particular for isolating specific sample regions thereof.

Microtomes are used solely in the preparation of microscopic samples. Microtomes may also comprise lasers for that purpose. The sections obtained by means of a microtome are applied to a slide, as mentioned above, optionally fixed thereto, stained, etc. Only then are they ready for use in the method according to the invention or in a corresponding examination system. A microtome is fundamentally different from a laser microdissection system in terms of its operation inter alia in that sections having as homogeneous a section thickness as possible are obtained therein. Microtomes are therefore designed to produce a large number of identical sections with parallel section surfaces, whereas laser microdissection systems are configured to remove dissectates according to sample-dependent criteria, for example according to visual criteria. A person skilled in the art would therefore not transfer technical solutions used in the case of microtomes to methods and examination systems which include the use of laser microdissection systems.

In FIG. 1, a method according to an embodiment of the invention is shown schematically and is designated generally 100.

In a first step 101 of the method 100, a slide 50 is referenced manually or at least partially automatically by means of a laser microdissection system, of which there are shown here, in highly simplified form, only a laser unit 11, which emits a laser beam 12, and an optical microscope 13 symbolized by a lens.

As described in detail hereinbefore, at least two reference markings 51 in the same or different forms are applied to a corresponding slide 50. This is carried out, for example, using the above-described ("fourth") position information data. Corresponding data relating to the reference markings 51 can be stored in a suitable file in the laser microdissection system or corresponding software.

In a step, which can also be carried out in parallel with or independently of, or before or after, the method according to the invention, a tissue block, for example embedded in paraffin, or a frozen tissue sample is processed to produce microscopic samples, for example is cut in a microtome.

Corresponding samples or sections (a section is here considered to be a sample) can be applied to slides 50 previously marked in step 101, or the production of the reference markings 51 in accordance with step 101 takes place after the sample has been applied. Step 102 shown in FIG. 1 illustrates this, the slide 50 here being shown with a corresponding sample 52 and the reference markings 51. In the example shown, the sample 52 comprises, for example, two tissue regions 521 and 522 which are to undergo more detailed examination. In step 102, further preparation of corresponding slides 50 with samples 52 applied thereto can be carried out. For example, staining, fixing, dewatering and the like can take place. For processing in laser microdissection systems designed specifically therefor, a corresponding sample 52 can also be covered, for example, by means of a membrane in step 102.

In a step 103, a digital image of the sample 52 prepared on the slide 50 and of the reference markings 51 is produced using the magnifying digital optical imaging device 20, for example using a slide scanner.

In a step 104, at least one image region of the image is defined, and first position information data, which indicate the position of the at least one image region in the image, are generated. The image region is here designated 41 and the image is designated 40. This can take place, for example, within the scope of an examination of a corresponding image 40 by a pathologist, who provides image regions 41 of a corresponding image that are of interest with a limiting line, and/or by automatic examination of corresponding digital images. In the example shown, the image region 41 is shown as a square, but it may also have any other desired form, as already described. The image region 41 corresponds in the example to a sample region in which the tissue region 521 is located. The digital image 40 can also be referenced, for example, to a reference point 42.

In a subsequent step 105, the reference markings 51 which were produced on the slide in step 101 and imaged in step 103 are at the same time identified in order to create reference points to the first position information data. As mentioned, the order of identification of the reference points and other detection steps is not important. On this basis, a suitable file, for example an XML file, is produced in step 105, for example. In the example shown, x,y coordinates are shown in step 105 for illustration. However, as mentioned, complex forms can also be defined in particular in respect of the image region 41. For the image region 41 (see step 104), the coordinates x,y are shown, and for the reference markings, the coordinates $x_1,y_1$ and $x_2,y_2$ are shown. All the position information can be related to the reference point 42 (see step 104), the coordinates of which are here shown as $x_0,y_0$.

In a step 106, the first and second position information data are supplied to the laser microdissection system 10, for example via a corresponding file and/or a corresponding transfer device.

In a subsequent step 107, a further examination and imaging acquisition of the slide 50 having the sample 52 and the reference points 51 is carried out in the laser microdissection system 10. There is used for this purpose an image acquisition device 14 of the laser microdissection system 10, an imaging beam path here being illustrated at 15. This can pass through the same optical microscope as the laser beam 12.

In a step 108, which is here shown together with step 107, the reference markings 51 of the slide 50 which were produced previously in the same or a different laser microdissection system 10 in step 101 are identified, so that a reference system for the processing of a corresponding sample 52 on a slide 50 again exists. On this basis, third position information data, which indicate the position of the reference markings 51 on the slide 50 which has been introduced into the laser microdissection system 10, and thus ultimately the position of the reference markings 51 in the laser microdissection system 10 itself, can be produced.

In a step 109 of the method according to the embodiment shown in FIG. 1, the first, second and third position information data are correlated as described hereinbefore, and a sample region 53 of the sample 52 which corresponds to the at least one image region 41 of the image 40 defined in step 106 is also processed in accordance with step 109. Because this always takes place on the basis of data which are related to one another by means of the reference markings 51, such processing is particularly reliable.

Figure 2:
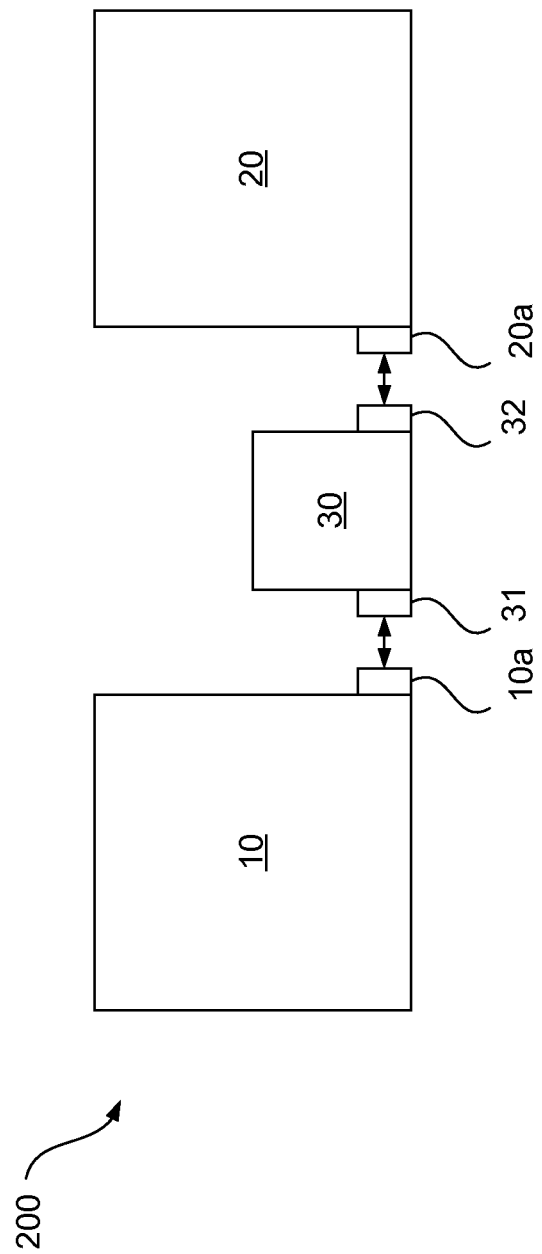
FIG. 2 schematically shows an examination system according to an embodiment of the invention.

In FIG. 2, an examination system according to an embodiment of the invention is shown schematically and designated generally 200. The individual elements of a corresponding examination system are shown in highly simplified form.

The examination system 200 comprises a magnifying digital optical imaging device 20 and a laser microdissection system 10. (The magnifying digital optical imaging device 20 and the laser microdissection system 10 each have suitable software.) A data transfer device 30 is provided for transferring data between the imaging device 20 and the laser microdissection system 10, namely in particular the first and second position information data or one or more corresponding files containing that data. The data transfer device 30 is provided with suitable interfaces 31 and 32 which allow the imaging device 20 and the laser microdissection system 10 to be connected. The imaging device 20 and the laser microdissection system 10 are also provided with suitable interfaces 10a and 20a for connection.

Figure 3:
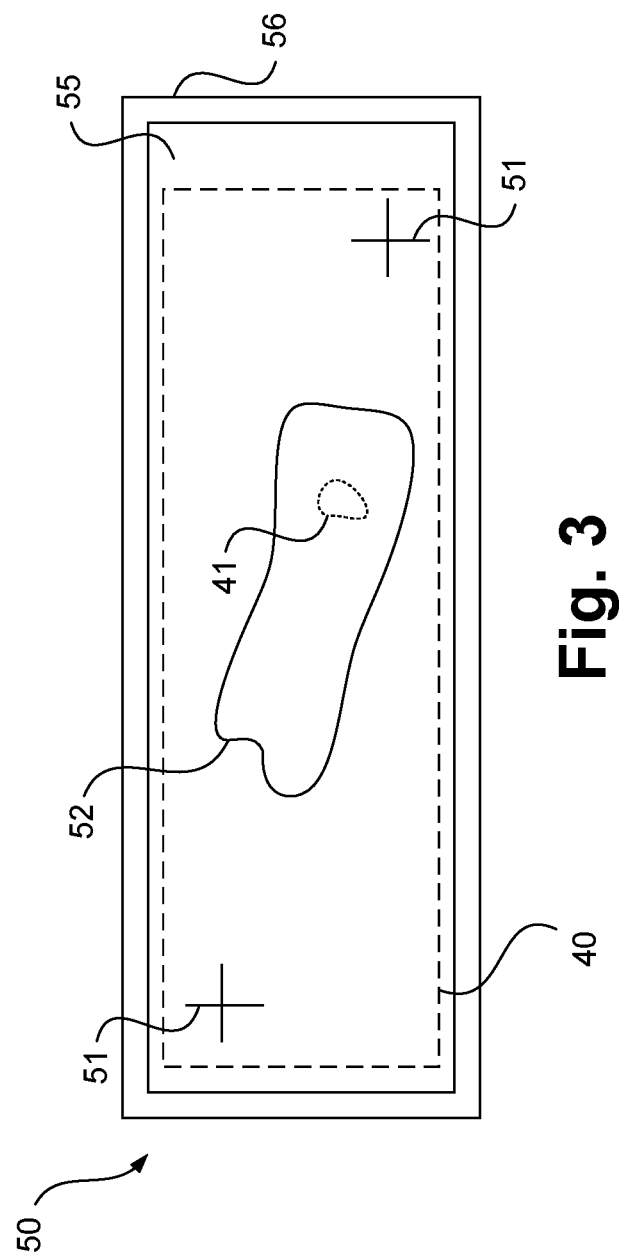
FIG. 3 schematically shows a slide marked in accordance with an embodiment of the invention.

In FIG. 3, a slide which is used in the context of the present invention and which is already marked is shown schematically and designated generally 50. The slide 50 is shown after the reference markings, which here too are designated 51, have been produced and after a sample 52 has been applied to the slide 50. In the example shown, the slide 50 comprises a membrane 55 to which the sample 52 is applied and in which the reference markings 51 are produced. The membrane 55 is secured in a suitable frame 56, for example a reusable steel frame.

Also shown in FIG. 3, by means of a dashed line, is a digital image 40 of the sample 52, which can be obtained by means of a digital optical imaging device 20 as is shown in FIG. 2. The production of a corresponding image 40 can include the production of an image of the sample 52 but also of the entire slide 50. In each case, however, the image 40 that is produced includes the reference markings 51. On a corresponding image, a pathologist can define at least one image region 41, for example an image region 41 having a property which is to be examined molecular-biologically and/or biochemically. In contrast to the example shown in FIG. 1, that region has an irregular form here. ("First") position information data generated within the context of the present invention indicate the position of the at least one image region 41 in the image 40. Further ("second") position information data indicate the position of the reference markings 51 in the image 40.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

10 Laser microdissection system
11 Laser unit
12 Laser beam
13 Optical microscope
14 Image acquisition system
15 Imaging beam path
20 Imaging device
30 Data transfer device
31, 32 Interfaces
10a, 20a Interfaces
50 Slide
51 Reference markings
52 Sample
521, 522 Tissue regions
53 Sample region
55 Membrane
56 Frame for membrane
40 Digital image
41 Image region
42 Reference point
100 Method according to the invention
101 First step
102 Second step
103 Third step
104 Fourth step
105 Fifth step
106 Sixth step
108 Eighth step
109 Ninth step
200 Examination system

The invention claimed is:

1. A method for examining a microscopic sample arranged on a slide using a magnifying digital optical imaging device, by which the sample is optically imaged and a digital image of the sample is produced, and for processing the microscopic sample arranged on the slide by a laser microdissection system which has an optical microscope and a laser and with which a laser beam for processing the sample is produced, the method comprising:

a) producing at least two reference markings on the slide by the laser beam of the laser microdissection system, the reference markings being identifiable both by the digital optical imaging device and by the laser microdissection system, b) applying the sample to the slide, before or after the reference markings are produced on the slide in accordance with step a), c) producing a digital image of the sample on the slide by the digital optical imaging device, wherein the image also includes the reference markings, d) defining at least one image region of the image and generating first position information data which indicate a position of the at least one image region in the image, e) identifying the reference markings in the image and generating second position information data which indicate a position of the reference markings in the image, before, during or after the at least one image region of the image is defined in accordance with step d), f) providing the first and second position information data to the laser microdissection system, g) imaging the slide having the sample and the reference markings and identifying the reference markings by the laser microdissection system, and generating third position information data which indicate the position of the reference markings in the laser microdissection system, and h) correlating the first position information data, the second position information data and the third position information data, and processing at least one sample region of the sample which corresponds to the at least one image region of the image defined in step d), by the laser microdissection system.

2. The method according to claim 1, wherein the at least two reference markings are produced in accordance with step a) by the laser microdissection system based on fourth position information data which specify a position of the reference markings on the slide.

3. The method according to claim 2, wherein the reference markings are identified in the image and/or the laser microdissection system using the fourth position information data.

4. The method according to claim 1, wherein the sample is imaged on an enlarged scale by optical components of the digital optical imaging device.

5. The method according to claim 1, wherein a slide is used which is made at least in part of glass, metal or plastics material and/or which has a membrane, and wherein the reference markings are produced in the glass, metal, plastics material and/or the membrane.

6. The method according to claim 1, wherein the identification of the reference markings in accordance with step e) and/or in accordance with step g) is carried out at least in part by a manual and/or automated method.

7. The method according to claim 1, wherein the at least one image region of the image is defined in accordance with step d) by manual and/or automatic drawing of a cut line that is to be used by the laser microdissection system.

8. The method according to claim 1, wherein the first position information data further describe a form and/or surface of the at least one image region of the image.

9. An examination system which is configured for examining and processing a microscopic sample arranged on a slide, the examination system comprising:

a magnifying digital optical imaging device configured to optically image the sample arranged on the slide and to produce a digital image of the sample;

a laser microdissection system which has an optical microscope and a laser configured to produce a laser beam for processing the sample; and a controller configured to control the digital optical imaging device and the laser microdissection system and to control, execute and/or operate the method according to claim 1.

10. The examination system according to claim 9, wherein the controller comprises software which is installed on the magnifying digital optical imaging device and/or the laser microdissection system.

11. The examination system according to claim 9, wherein:

a) the laser microdissection system is configured to produce, by the laser beam, at least two reference markings on the slide, the at least two reference markings being identifiable both by the digital optical imaging device and by the laser microdissection system, b) the sample is applied to the slide, and the system is configured to provide for the application to take place before or after the reference markings are produced on the slide in accordance with feature a), c) the digital optical imaging device is configured to produce a digital image of the sample on the slide, wherein the image also includes the reference markings, d) the digital optical imaging device is configured to define at least one image region of the image and to generate first position information data which indicate the position of the at least one image region in the image, e) the digital optical imaging device is further configured to identify the reference markings in the image and to generate second position information data which indicate a position of the reference markings in the image before, during or after the at least one image region is defined in accordance with feature d), f) the examination system is configured to provide the first and second position information data to the laser microdissection system, g) the laser microdissection system is configured to image the slide having the sample and the reference markings and to identify the reference markings, and to generate third position information data which indicate a position of the reference markings in the laser microdissection system, and h) the laser microdissection system is configured to correlate the first position information data, the second position information data and the third position information data and to process at least one sample region of the sample which corresponds to the at least one image region of the image defined in feature d).

12. The examination system according to claim 9, further comprising a data transfer device configured to provide the first and second position information data to the laser microdissection system.

13. The method of claim 1, wherein the digital optical imaging device is remote from the laser microdissection system such that the slide is in a first location when the digital image is produced with the digital optical imaging device and the slide is in a second location when imaged by the laser microdissection system, the first location being remote from the second location.

14. The method according to claim 13, wherein the processing of the at least one sample region of the sample in step h) comprises cutting the sample with the laser beam of the laser microdissection system while the sample is mounted on the slide.

15. The method according to claim 13, wherein the processing of the at least one sample region of the sample in step h) comprises cutting, with the laser beam of the laser microdissection system and while the sample is mounted on the slide, the sample region based on the correlated first, second, and third position information data.

16. The method according to claim 13, wherein the processing of the at least one sample region of the sample in step h) comprises cutting, with the laser beam of the laser microdissection system and while the sample is mounted on the slide, the sample region out from the sample based on the correlated first, second, and third position information data.

17. The method according to claim 16, wherein the image region maps directly onto the sample region and step b) comprises applying the sample to the slide after the reference markings are produced on the slide in accordance with step a);

the slide being formed from glass, metal, and/or plastic material and the reference markings comprise cuts defined therein.

18. A non-transitory computer readable medium having instructions thereon, which upon execution by one or more processors, causes the one or more processors to control, execute and/or operate a method for examining a microscopic sample arranged on a slide using a magnifying digital optical imaging device, by which the sample is optically imaged and a digital image of the sample is produced, and for processing the microscopic sample arranged on the slide by a laser microdissection system which has an optical microscope and a laser and with which a laser beam for processing the sample is produced, the method comprising:

a) producing at least two reference markings on the slide by the laser beam of the laser microdissection system, the reference markings being identifiable both by the digital optical imaging device and by the laser microdissection system, b) applying the sample to the slide, before or after the reference markings are produced on the slide in accordance with step a), c) producing a digital image of the sample on the slide by the digital optical imaging device, wherein the image also includes the reference markings, d) defining at least one image region of the image and generating first position information data which indicate a position of the at least one image region in the image, e) identifying the reference markings in the image and generating second position information data which indicate a position of the reference markings in the image, before, during or after the at least one image region of the image is defined in accordance with step d), f) providing the first and second position information data to the laser microdissection system, g) imaging the slide having the sample and the reference markings and identifying the reference markings by the laser microdissection system, and generating third position information data which indicate the position of the reference markings in the laser microdissection system, and h) correlating the first position information data, the second position information data and the third position information data, and processing at least one sample region of the sample which corresponds to the at least one image region of the image defined in step d), by the laser microdissection system.

\* \* \* \* \*